United States Patent [19]
Ross et al.

[11] Patent Number: 6,083,214
[45] Date of Patent: Jul. 4, 2000

[54] MEDICANT DISPERSING METHOD

[76] Inventors: Jesse Ross; David M. Ross, both of 382 E. Shore Rd., Great Neck, N.Y. 11023-2420

[21] Appl. No.: 09/170,728

[22] Filed: Oct. 13, 1998

[51] Int. Cl.[7] ................................................. A61M 31/00
[52] U.S. Cl. .............................. 604/500; 604/20; 604/28; 607/46; 607/2
[58] Field of Search ...................... 604/500, 506, 604/507, 508, 512, 28, 30, 20; 607/72, 2, 46, 71

[56] References Cited

U.S. PATENT DOCUMENTS

| | | | |
|---|---|---|---|
| 3,043,310 | 7/1962 | Milinowski | 607/71 |
| 4,509,521 | 4/1985 | Barry | 607/46 |
| 4,537,195 | 8/1985 | McDonnell | 607/46 |
| 4,856,526 | 8/1989 | Liss et al. | 607/46 |
| 4,889,526 | 12/1989 | Rauscher et al. | 600/14 |
| 5,718,721 | 2/1998 | Ross | 607/46 |

*Primary Examiner*—Corrine McDermott
*Assistant Examiner*—Kent Gring
*Attorney, Agent, or Firm*—Myron Amer P.C.

[57] ABSTRACT

A treatment of using pressure-driven blood infused with an antibiotic, analgesic or like pharmacological agent from a site of delivery to the patient to a site of pain or ache, in which significantly the noted blood movement is according to an established pressure gradient and supplements the pumping function of the heart, to thereby lessen the time interval of travel between the two sites.

1 Claim, 2 Drawing Sheets

MEDICANT DISPERSING METHOD

The present invention relates generally to improvements in providing a more rapid therapeutic effect of antibiotics, analgesics, gene replacement and other pharmacological agents, hereinafter individually and collectively designated "medicants" in relation to a medicant treatment-requiring affected site or source of pain in a human body, the improvements, more particularly, with respect to medicants either intravenously, orally, inhaling, topically or otherwise received, rendering a therapeutic effect in significantly less time than heretofore.

As an example, it is known that the medicant ergotamine tartrate is the drug of choice to relieve a headache of migraine, and also known by common experience, that it typically takes an hour for the drug to have its intended end result of relieving the pain of a headache of migraine.

Broadly, it is an object of the present invention to provide a medicant-dispersing method overcoming the foregoing and other shortcomings of the prior art.

More particularly, it is an object to establish a pressure gradient in the blood of a circulatory system of a patient to pressure-drive medicant-infused blood more rapidly to an effected site or source of pain, all as will be better understood as the description proceeds.

The description of the invention which follows, together with the accompanying drawings should not be construed as limiting the invention to the example shown and scribed because those skilled in the art to which this invention appertains will be able to devise other forms thereof within the ambit of the appended claims.

Figure 1:
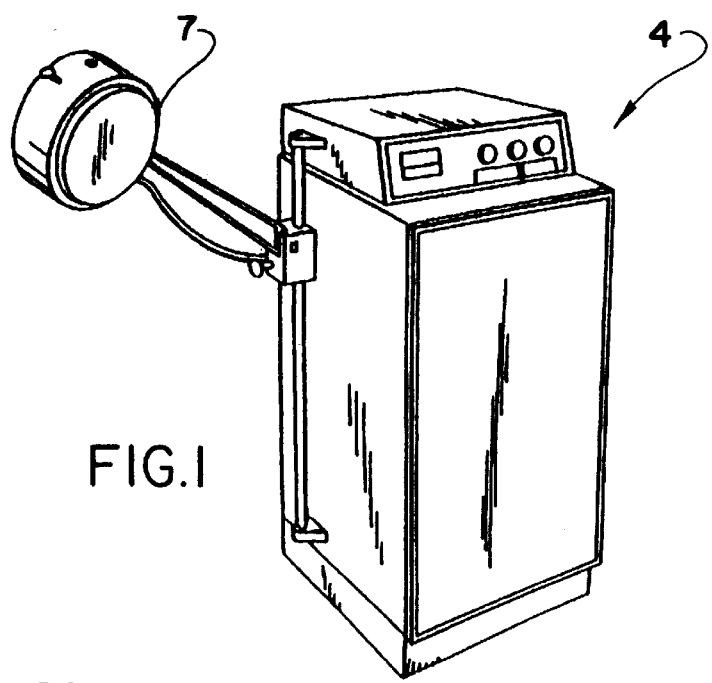
FIG. 1 is a perspective view of an apparatus for generating an electromagnetic field for practicing the within inventive method.

Underlying the present invention is the recognition that the pumping function of the heart produces blood flow following the formula PV equals a constant and that said blood is directional, namely from the aorta 10 to the vena cava 11. Using these blood flow parameters to advantage, the within inventive method at an affected site or source of pain diminishes the pressure thereat so that in relation to an upstream site having an unchanged pressure, there is a pressure gradient which pressure-drives the blood more forcefully than the heart itself, and consequently medicant-infused blood is more rapidly delivered to an affected site or source of pain.

The generated electromagnetic field of apparatus 4 can be used to advantage to relieve migraine headache patient-experienced pain, not by directly treating the source of pain, as at the patient's parietal lobe 12, but by causing a more rapid flow of medicant, i.e., in this described example ergotamine tartrate, infused in the patient's blood to be pressure-driven to the affected site or source of pain 12.

To the above end, to a patient 14 the head 7 of apparatus 4 is positioned in electromagnetic field penetrating relation to a selected first site body location 12 of the patient at which the blood flow parameters are governed or follow the formula pressure P times velocity V equals a constant in the directional flow F in the patient's circulatory system 13.

Figure 2:
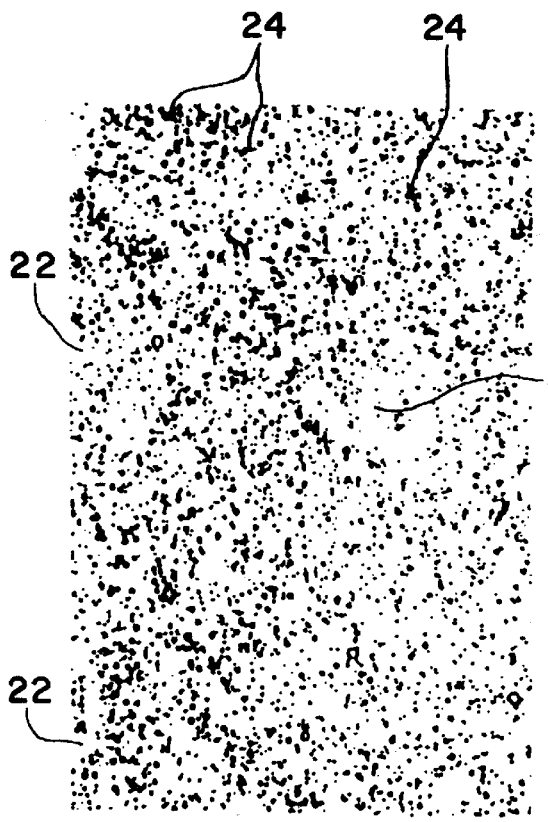
FIG. 2 is an illustration of a microphotograph of blood prior to the subjection to high frequency oscillation.
Figure 3:
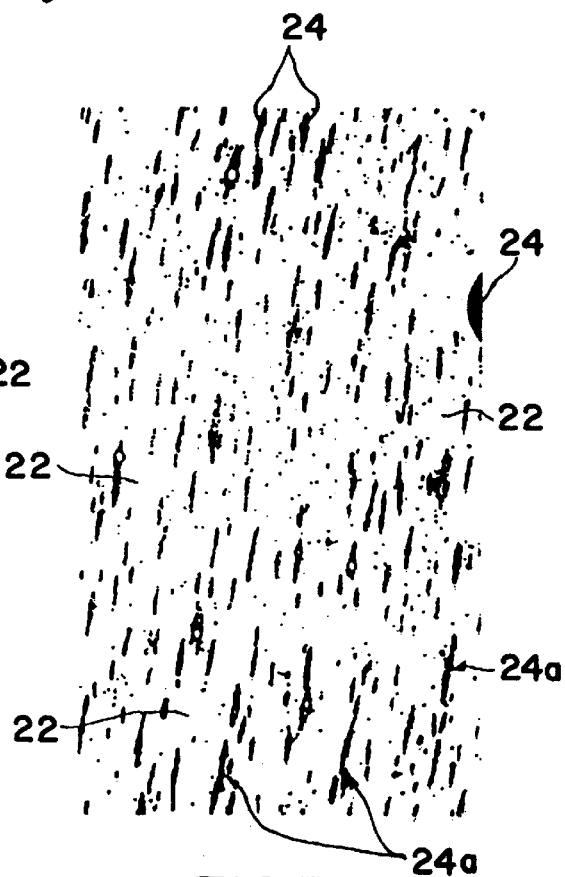
FIG. 3 is another microphotograph illustration of the blood of FIG. 2, but after subjection to the high frequency oscillation and showing a pearl chain formation of the nutritive blood elements.
Figure 4:
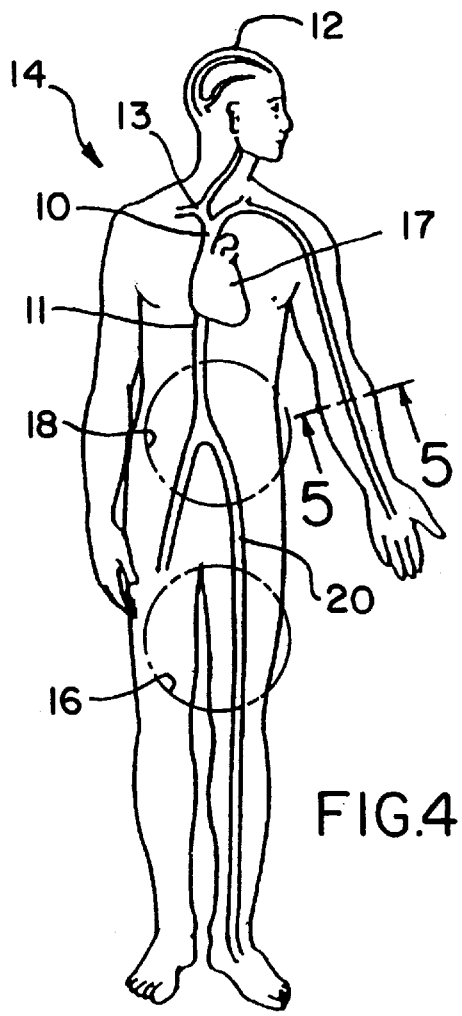
FIG. 4 is a graphic of blood circulation.
Figure 5:
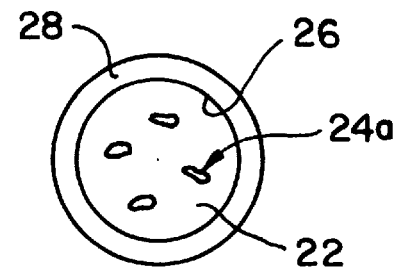
FIG. 5 is a sectional view of the brachial artery as taken along line 5—5 of FIG. 4.
Figure 6:
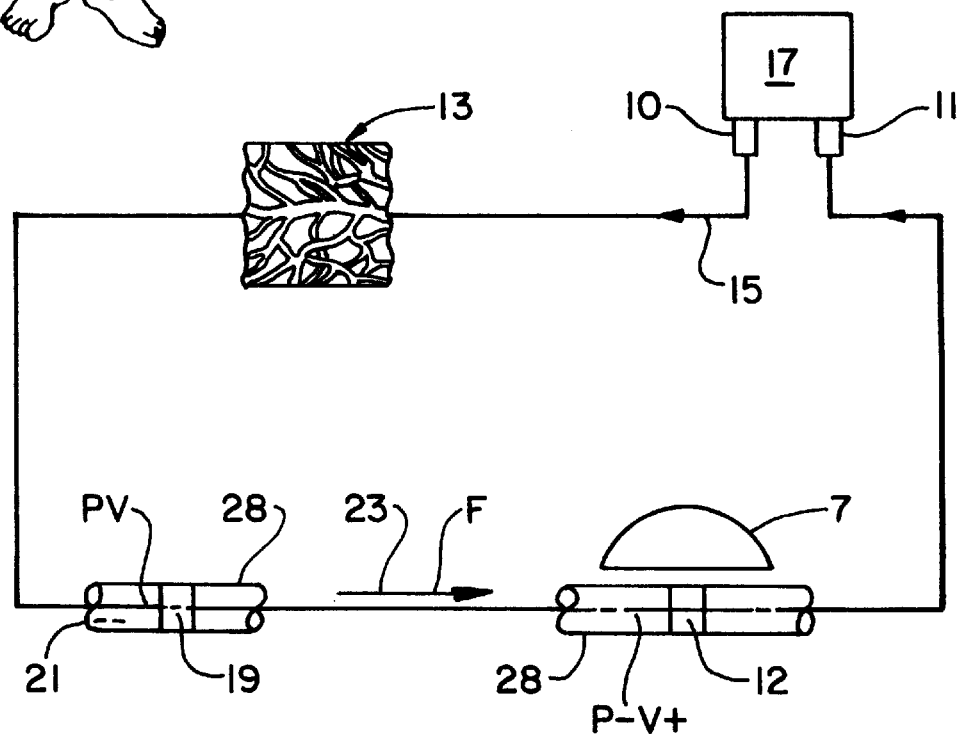
FIG. 6 is a diagramatic flow diagram of the application of the within inventive method to a circulatory system of a patient.

The result of the impingement of the electromagnetic field on the blood is best understood from FIGS. 2 and 3, to which reference should now be made. Blank or unoccupied areas, individually and collectively designated 22 will be understood to be the fluid content of the blood, and the occupied areas, also individually an collectively designated 24, will be understood to be the nutritive elements of which the blood is composed, such as lymph, chyle, plasma, etc.

By comparison of FIG. 2 before subjection to the electromagnetic field, to FIG. 3 after subjection, it should be readily observable that the pattern of FIG. 2 is a random dispersion of the blood fluid and nutritive elements contents 22, 24, and that in FIG. 3 the nutritive elements 24 have assumed a chain-like formation, more particularly designed 24A, which formulation is known in the parlance of the art as a "pearl chain" formulation.

A physical noteworthy attribute provided by the pearl chain formation 24A is its longitudinal orientation which during blood flow in the longitudinal direction 15 is with minimum resistance at the interface 26 of the blood 22, 24 and the interior cell wall or cell membrane 28. This manifests itself as an increased velocity V+ and a correspondingly diminished pressure P−, or the formula denoting blood flow as P− times V+ equals a constant.

Next, a second site is selected between the aorta 10 and vena cava 11 of the patient's heart or blood-pumping muscle 17. The basis of selection of the body location 19 is to make accessible a main artery of the patient's circulatory system. Preferred locations that have provided good results in practice is location 16 which will be understood to be the interior portion of the thigh i.e., femoral area, and location 18 which will be understood to be the descending colon, both locations 16 and 18 being on or adjacent to the anterior tibial 20 and, more importantly, in an upstream location relative to the affected site 12 or source of pain.

At the second site 19, the medicant is appropriately introduced into the patient's circulatory system 13 and flows therethrough in relation to the interior cell wall or cell membrane 28 in a random dispersion of the blood fluid and nutritive elements contents 22, 24 as depicted in FIG. 2. Thus at site 19, there is no modification of the flow parameters of pressure P times velocity V equals a constant. As between the upstream pressure P and the downstream pressure P−, there is thus established a pressure gradient which supplement the pumping function of the heart 17 to pressure-drive, as denoted by the arrow 20, the medicant-infused blood 21 from second site 19 to first site 17 wherein, in practice under the circumstances described, the patient 14 felt relief from the headache of migraine in significantly less time than the prior treatment without an established pressure gradient and relying only on the pumping function of the patient's heart 17.

For completeness sake, it is noted that in the treatment use of the apparatus 4, the electromagnetic field utilized might typically have the following specific parameters:

1. A frequency of 27.12 megahertz (11 meter band);
2. A pulse repetition rate of 80 to 600 pulses per second;
3. A pulse width of 65 microseconds;
4. A power range, per pulse, of between 293 and 975 watts;
5. A duty cycle between ½ of 1% to 3.9%; and
6. A square pulse, with a rise and fall time less than 1%.

While the apparatus for practicing the within inventive method, as well as the method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method of reducing the time duration of dispersing a medicant to a site of an internal injury of a patient, said time duration-reducing method comprising the steps of using the directional flow of blood through a circulatory system of arteries and veins of a patient proceeding from said patient's aorta to said patient's vena cava, identifying a first site of a medicant treatment-requiring injury of said patient, determining the position of said first site relative to said patient's aorta, identifying a second site between said patient's aorta and said first site, medicant-introducing at said second site a selected medicant into said patient's circulatory system having blood flow at a specific pressure and specific velocity, using an electromagnetic field at said second site effective to produce elongated shapes of blood cells of said patient's blood to contribute to a velocity exceeding said first site specific velocity and a corresponding diminished pressure relative to said first site specific pressure, whereby said pressure gradient of said specific pressure upstream of said diminished pressure produces the delivery of said medicant by blood flow from said first site to said second site.

* * * * *